United States Patent [19]

Hammond

[11] 4,334,109

[45] Jun. 8, 1982

[54] SYNTHESIS OF 4-HALOALKYL ALCOHOLS

[75] Inventor: Kenneth G. Hammond, Poughkeepsie, N.Y.

[73] Assignee: Texaco Inc., White Plains, N.Y.

[21] Appl. No.: 1,241

[22] Filed: Jan. 5, 1979

[51] Int. Cl.$^3$ .................... C07C 29/64; C07C 31/36
[52] U.S. Cl. .................................................. 568/841
[58] Field of Search ........................................ 568/841

[56] References Cited

U.S. PATENT DOCUMENTS 2,491,834  12/1969  Scott .................................. 260/657
2,889,380  6/1959  Hamel ................................ 568/841

FOREIGN PATENT DOCUMENTS 4418841  8/1969  Japan .................................. 568/841

OTHER PUBLICATIONS

Starr et al., J. Am. Chem. Soc., 56 (1934) 1595–1596.

*Primary Examiner*—Howard T. Mars
*Attorney, Agent, or Firm*—Carl G. Ries; Robert A. Kulason; Henry W. Archer

[57] ABSTRACT

Disclosed is a process for preparing 4-haloalkyl alcohols by reacting tetrahydrofuran derivatives and hydrogen halides in the presence of a resinous quaternary ammonium halide catalyst, preferably styrene-divinyl benzene copolymer resins having pendant $N(R)_3X$, where X is halogen, or $N(R)_2$ groups of tetrahydrofuran. The haloalcohols are useful intermediates for the preparation of dyes, halogenated polymers, pharmaceuticals, polymerization catalysts and plasticizers.

6 Claims, No Drawings

SYNTHESIS OF 4-HALOALKYL ALCOHOLS

FIELD OF THE INVENTION

This invention relates to an improved process for synthesizing 4-haloalcohols from tetrahydrofuran derivatives and hydrogen halides in the presence of a resin quaternary ammonium halide catalyst.

Description of the Prior Art

The prior art to which this invention relates is aware, inter alia, of the following disclosures. Among these, D. Starr and R. M. Hixon, J. Amer. Chem. Soc. 56, 1596 (1934), were first to report that 4-chlorobutanol can be prepared from tetrahydrofuran and hydrogen chloride. Their procedure employs no catalyst and has been the most widely used method of preparation of this alcohol since the mid 1930's.

Several authors have reported that zinc chloride will catalyze the formation of 4-chlorobutanol from tetrahydrofuran and hydrogen chloride. The earliest references found are: M. Servigne, E. Szarvasi, and L. Neuvy, Compt. rend., 241, 936-964 (1955), Chem. Abst. 50, 1063g (1956) and British Pat. No. 788,349 (to l'Air Liquide), Dec. 23, 1957 Chem. Abst., 52, 1188d (1958).

N. D. Scott, U.S. Pat. No. 2,491,834 issued Dec. 20, 1949, describes a reaction of tetrahydrofuran with hydrogen chloride in the presence of quaternary ammonium chloride catalysts (tertiary amine hydrochlorides and low molecular weight tetraalkyl ammonium chlorides). In this reaction, 1,4-dichlorobutane, not 4-chlorobutanol was the product formed.

The present process differs from the above mentioned references in that it uses a resin quaternary ammonium halide or amine catalyst which unexpectedly increases the rate of product formation. As regards the use of zinc chloride, such a composition is functionally different from the catalysts used herein. Also zinc chloride is soluble in the haloalcohol and therefore is more difficult to remove from the product that is the insoluble resin quaternary halide.

The principal object of this invention is to provide an improved synthesis of 4-haloalcohols characterized by increased yields and reduced reaction times.

Additional objects and advantages of the invention will be set forth in part in the description which follows and in part will be obvious from the description, or may be realized by practice of the invention, the objects and advantages being realized and attained by means of the methods, processes, instrumentalities and combinations particularly pointed out in the appended claims.

SUMMARY OF THE INVENTION

The synthesis of the invention involves the use of a resin catalyst which is of the type exemplified by "Amberlyst 26", and "Amberlyst 21", both sold by Rohm and Haas, Inc. The first is a styrene-divinyl-benzene copolymer resin with pendant $N(Me)_3Cl$ groups and the second is a similar resin with pendant $N(Me)_2$ groups. However, any insoluble polymeric composition which is not degraded under the reaction conditions, and which carries pendant $N(R)_3X$, where X is chlorine, bromine or iodine or $N(R)_2$ groups, wherein R is an alkyl group having from 1 to 10 carbons, is suitable for use in this invention.

The synthesis of the invention is governed by the following equilibrium expression:

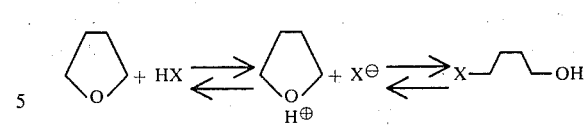

where X is chloride, bromide or iodide. The function of the catalyst is to provide a greater concentration of halide ion than would be present when no catalyst is employed. The increased concentration of halide ion in the medium results in a reduction of the time period necessary to establish equilibrium when the cyclic ether and the hydrogen halide are the initial components present. The quaternary salt functionality of the polymer resin is chosen to correspond with the hydrogen halide that is to be used. Thus polymer resins with pendant $N(R)_3Cl$ groups, such as "Amberlyst 26", are used with hydrogen chloride in the preparation of chloroalcohols. Similarly, resins with pendant $N(R)_3Br$ groups and those with pendant $N(R)I$ groups are used with substantially equivalent results with hydrogen bromide and hydrogens iodide, respectively, in the preparation of the corresponding bromo and iodoalcohols. Polymer resins which have a pendant amine functionality (resin-$N(R)_2$), such as "Amberlyst 21", react with hydrogen halides to form the corresponding ammonium halide salts (resin-$NH(R)_2X$). This type resin is therefore used with hydrogen chloride, hydrogen bromide and hydrogen iodide in order to form the corresponding chloro, bromo and iodoalcohols respectively. Polymer-bonded quaternary ammonium salts and amine catalysts are preferred because these are available in pellet form, are insoluble in the reaction medium, and are therefore easily recoverable. Soluble catalysts are less desirable because they are more difficult to separate from the product. Polymeric resins catalysts that are not degraded under the reaction conditions are chosen, and therefore can be reused many times.

Examples of preparations of 4-chlorobutanol carried out both with and without catalyst are given below. Two groups of experiments, conducted under somewhat different reaction conditions, are summarized. In each of the examples samples of the reaction mixture were removed at intervals and analyzed for 4-chlorobutanol. The process of haloalcohol formation (% conversion of THF into alcohol=mole alcohol (100/mole original THF) as a function of reaction time for each example is recorded in Table I. From the data it is apparent that alcohol formation occurs significantly faster when the catalyst is employed. In the catalyzed reaction, the most important single factor which determines the actual minimum reaction time is the hydrogen chloride charge rate. The present method appears to be the best procedure with respect to product quality, reaction time, ease of catalyst removal and cost of raw materials, for the preparation of 4-chlorobutanol.

The invention therefor is further illustrated in non-limiting fashion by the following examples.

EXAMPLE I

Tetrahydrofuran (432 gr., 6.0 mole) and "Amberlyst-26" (43 gr.) were charged to a 1.0 liter flask equipped with an stirrer, a thermometer, a sparger, an efficient condenser and a heating mantle. The mixture was heated at refulx as anhydrous HCl was charged at approximately 2.8 moles/hr. for 2.5 hr. The mixture was then filtered to remove the insoluble catalyst. A sample removed from the flask after 1.5 hr. (25 gr) and the product after 2.5 hr. (660 gr.) were analyzed immediately for % conversion of THF into 4-chlorobutanol by NMR.

EXAMPLE II

Tetrahydrofuran (432 gr., 6.0 moles) was treated with HCl under the conditions described above. However no catalyst was used in this run. A sample removed from the flask after 1.5 hr. (25 gr.) and the product after 2.5 hr. (491 gr.) were analyzed immediately for % conversion by NMR. The final product in this example contained a small amount of 4-chlorobutanol but was primarily a physical mixture of THF and HCl.

Examples III, IV, V, VI, which follow were conducted at a lower temperature and at a lower HCl charge rate than those described above. These conditions were used in order to minimize the loss of volatile THF through the condenser system. Longer reaction times were necessary because of the reduced HCl charge rate.

EXAMPLE III

For this Example, tetrahydrofuran (1874 gr., 26.0 moles) and "Amberlyst-26" (170 gr.) were charged to a 5.0 liter flask equipped with a condenser, heating mantel, thermometer, sparger, and stirrer. The mixture was warmed to about 50° C. The heat source was turned off and HCl gas was charged at approximately 6.5 moles/hr. for a 5.0 hr. period during which time the pot temperature rose to 87° C. The resin was removed from the mixture by filtration in order to yield 2949 gr. of product. During the course of the reaction small samples of the mixture were removed at intervals and analyzed for % conversion of THF into 4-chlorobutanol by NMR.

EXAMPLE IV

Tetrahydrofuran (1874 gr., 26.0 moles) and "Amberlyst-26" (170 gr., recycled from Example III) were charged to a 5.0 liter equipped as in Example III, and the mixture was stirred at room temperature. HCl gas was charged to the mixture at approximately 6.5 moles/hr. for a 6.0 hr period during which time the pot temperature rose to 87° C. The resin was removed from the mixture by filtration in order to yield 2886 gr. of product. During the course of the reaction small samples of the mixture were removed at intervals and analyzed for % conversion of THF into 4-chlorobutanol.

EXAMPLE V

Tetrahydrofuran (1874 gr., 26.0 moles) and "Amberlyst-26" (562 gr.) were charged to a 5.0 liter flask, equipped as in Example III, and the mixture was warmed to about 50° C. The heat source was turned off and HCl gas was charged at approximately 6.5 moles/hr. for a 5.0 hr. period during which time the pot temperature rose to 86° C. The resin was removed from the mixture by filtration in order to yield 2886 gr. of product. During the course of the reaction small samples of the mixture were removed at intervals and analyzed for % conversion of THF into 4-chlorobutanol.

EXAMPLE VI

Tetrahydrofuran (1874 gr., 26.0 moles) was charged to a 5.0 liter flask, equipped as in Example III, and the mixture was stirred at room temperature. The HCl gas was charged at approximately 6.5 moles/hr., for a 6.0 hr. period during which time the pot temperature rose to 60° C. The reaction mixture was filtered to yield 2682 gr., of a solution which contained some 4-chlorobutanol but was primarily a physical mixture of THF and HCl.

TABLE I

| % CONVERSION OF TETRAHYDROFURAN INTO 4-CHLOROBUTANOL | | | | | | |
|---|---|---|---|---|---|---|
| EXAMPLE NUMBER | I | II | III | IV | V | VI |
| Tetrahydrofuran charge (moles) | 6.0 | 6.0 | 26.0 | 26.0 | 26.0 | 26.0 |
| "Amberlyst-26" charge (grams) and condition | 34-New | None | 170-New | 170-Used | 562-New | None |
| HCl charge rate moles/hour | 2.8 | 2.8 | 6.5 | 6.5 | 6.5 | 6.5 |
| % Conversion of THF into 4-chlorobutanol at the specified reaction time:[1] | | | | | | |
| 1.5 Hours | 45.9 | 5.8 | | | | |
| 2.0 Hours | — | — | 22.0 | — | 28.1 | 8.2 |
| 2.5 Hours | 76.6 | 11.4 | | | | |
| 3.0 | | | | | | |
| 3.5 | | | | | | |
| 4.0 | | | 74.3 | — | 72.0 | — |
| 4.5 Hours | | | | | | |
| 5.0 Hours | | | 82.5 | 79.6 | 78.7 | 29.0 |
| 5.5 Hours | | | | | | |
| 6.0 Hours | | | — | 86.5[2] | — | 44.4 |

[1]Approximately 0.5 ml of each reaction mixture was treated with excess trichloroacetyl isocyanate. The % conversion of the THF into 4-chlorobutanol was calculated from the NMR spectrum of the resulting mixture.
[2]GC analysis indicated that this product contained: 87.1 wt % 4-chlorobutanol, 5.6 wt % THF, 3.5 wt % HCl, and 3.8 wt % unidentified materials.

In all of the examples, 9 to 30 parts by weight of resin per 100 parts by weight of THF were used. However, alcohol formation proceeds at a satisfactory rate in cases where a small amount (for example 1.0 gr catalyst per 100 gr THF) or a larger amount of catalyst is used.

The resin catalysts of this invention can be employed in a batch process as is described in the Examples or can be employed in a continous process.

It should be noted that excess hydrogen halide was employed in all of Examples. Under optimum conditions 1.0–1.2 moles of HCl per mole of THF should be used (as in Example 1). The use of this HCl/THF mole ratio results in a satisfactory yield of alcohol and minimizes HCl loss. The use of a large excess of HCl would probably increase the amount of side products formed (particularly 1,4-dichlorobutane). All of the samples of 4-chlorobutanol cited in the example preparations were contaminated with small amounts THF, HCl, and unidentified materials. These samples of the haloalcohol were satisfactory for the preparation of intermediates and therefore no purification was attempted.

If desired, the haloalcohol can be further refined by distillation, chromatography or other methods of purification well known in the art.

The invention is not restricted to any of the specific examples described, for it is intended to cover variations encompassed by the scope of the invention and to claim all inherent novelty thereof.

What is claimed is:

1. A process for synthesizing a chlorobutanol comprising reacting at a temperature of 20° to 87° C. tetrahydrofuran and hydrogen chloride in the presence of 1 to 30 parts by weight per 100 parts by weight of tetrahydrofuran of a polymeric resin which is not degraded under the reaction conditions having pendant $N(R)_3X$ or $N(R)_2$ groups where R is an alkyl group having from 1 to 10 carbon atoms and where X is chloride, bromide or iodide; said resin being insoluble in said 4-chlorobutanol.

2. The process of claim 1 wherein the said resin is a styrene-divinylbenzene copolymer having pendant trimethyl ammonium chloride groups.

3. The process of claim 1 wherein said resin is a styrene-divinylbenzene copolymer having pendant dimethylamino groups.

4. The process of claim 1 wherein there is employed an amount of hydrogen chloride ranging from 1.0 to 1.2 mole per mole of tetrahydrofuran.

5. The process of claim 1 wherein there is employed from 9 to 30 parts by weight of resin per 100 parts by weight of tetrahydrofuran.

6. The process of claim 1, wherein said resin is in pellet form.

* * * * *